(12) United States Patent
Sosnowska-Turek et al.

(10) Patent No.: US 10,166,262 B2
(45) Date of Patent: Jan. 1, 2019

(54) STRAIN OF BACTERIA AND COMPOSITION COMPRISING THE SAME

(71) Applicants: Ewelina Sosnowska-Turek, Olsztyn (PL); Jaroslaw Piotr Turek, Olsztyn (PL)

(72) Inventors: Ewelina Sosnowska-Turek, Olsztyn (PL); Jaroslaw Piotr Turek, Olsztyn (PL)

( * ) Notice: Subject to any disclaimer, the term of this patent is extended or adjusted under 35 U.S.C. 154(b) by 0 days.

(21) Appl. No.: 15/492,563

(22) Filed: Apr. 20, 2017

(65) Prior Publication Data
US 2018/0303884 A1 Oct. 25, 2018

(51) Int. Cl.
| | | |
|---|---|---|
| *A61K 39/02* | (2006.01) | |
| *A61K 35/747* | (2015.01) | |
| *C12N 1/20* | (2006.01) | |
| *A23L 33/135* | (2016.01) | |

(52) U.S. Cl.
CPC .......... *A61K 35/747* (2013.01); *A23L 33/135* (2016.08); *C12N 1/20* (2013.01); *A23V 2002/00* (2013.01)

(58) Field of Classification Search
None
See application file for complete search history.

(56) References Cited

U.S. PATENT DOCUMENTS

| 5,705,160 | A | * | 1/1998 | Bruce | .................. | A61K 35/747 424/93.45 |
|---|---|---|---|---|---|---|
| 6,761,885 | B1 | | 7/2004 | Hakansson et al. | | |
| 2013/0084623 | A1 | | 4/2013 | Zielinska et al. | | |

FOREIGN PATENT DOCUMENTS

| CN | 104830731 A | 8/2015 |
|---|---|---|
| EP | 0353581 A2 | 2/1990 |
| EP | 2311473 A1 | 4/2011 |
| KR | 20110094832 A | 8/2011 |
| KR | 20130032558 A | 4/2013 |
| PL | 179838 B1 | 11/2000 |
| PL | 195089 B | 8/2007 |
| PL | 214583 B1 | 8/2013 |
| WO | 8905849 A1 | 6/1989 |
| WO | 2007003917 A1 | 1/2007 |
| WO | 2009/068474 A1 | 6/2009 |
| WO | 2009138092 A1 | 11/2009 |

OTHER PUBLICATIONS

Li et al (Innovative Food Science and Emerging Technologies. 2005. 6(2): 125-133).*
European Search Report completed Apr. 6, 2017, from EP Application No. EP16460032, 6 sheets.
Polish Search Report dated Jun. 20, 2016, from Polish Application No. PL414701, 1 sheet.
De Vries M. C. et al., "Lactobacillus plantarum—survival, functional and potential probiotic properties in the human intestinal tract", International Dairy Journal, Sep. 1, 2006 (Sep. 1, 2006), pp. 1018-1028, vol. 16, No. 9, doi:10.1016/J.IDAIRYJ.2005.09.003, ISSN 0958-6946, XP024963305 [A] 1,2.
Foligné B. et al., "Probiotics from research to market: the possibilities, risks and challenges", Current Opinion in Microbiology, GB, (Jul. 15, 2013), vol. 16, No. 3, Jul. 15, 2013 (Jul. 15, 2013), pp. 284-292, doi:10.1016/j.mib.2013.06.008, ISSN 1369-5274, XP055361497 [A] 1,2.
Seddik H. A. et al, "Lactobacillus plantarum and Its Probiotic and Food Potentialities", Probiotics and Antimicrobial Proteins, New York, NY; 2017, vol. 9, pp. 111-122, Heidelberg : Springer, (Mar. 7, 2017), doi:10.1007/s12602-017-9264-z, ISSN 1867-1306, XP055361504 [T] 1,2.
Parente E. et al. "Diversity of stress tolerance in Lactobacillus plantarum, Lactobacillus pentosus and Lactobacillus paraplantarum: a multivariate screening study", International Journal of Food Microbiology, (2010), vol. 144, pp. 270-279, XP027526626.
Tanganurat W. et a;. "Genotypic and phenotypic characterization of Lactobacillus plantarum strains isolated from Thai fermented fruits and vegetable", Journal Basic Microbiology, (2009), vol. 49, pp. 377-385.
Shah N. P., "Functional cultures and health benefits", International Dairy Journal, (2007), vol. 17, doi:doi:10_1016/j.dairyj.2007.01. 014, pp. 1262-1277, XP022261744.
Tuohy K. M. et al., "Using probiotics and prebiotics to improve gut health", Drug Discovery, (2003), vol. 8, doi: doi:10.1016/S1359-6446(03)02746-6, pp. 692-700, XP002496034.
Kesarcodi-Watson A. et al., "Probiotics in aquaculture: The need, principles and mechanisms of action and screening processes", Aquaculture, (2008), pp. 1-14, vol. 274, doi:doi:10.1016/j.aquaculture. 2007.11.019, XP022404840.
Verschuere L et al. "Protection of Artemia against the pathogenic effects of Vibrio proteolyticus CW8T2 by selected bacterial strains", Applied and Environmental Microbiology, (2000), pp. 1139-1146, vol. 66.
Verschuere L. et al., "Probiotic bacteria as biological control agents in aquaculture", Microbiology and Molecular Biology Review, (2000), pp. 655-671, vol. 64, doi:doi:10.1128/MMBR.64.4.655-671. 2000, XP009085480.
Biedrzycka E; Markiewicz L. H.; Bielecka M.; Siwicki A. K, "Shaping the micro ecosystem of gastrointestinal tract", Biedrzycka E; Markiewicz L. H.; Bielecka M.; Siwicki A. K., Zabielski R., Wydawnictwo Rolne I Lesne, Development control of gastrointestinal system in newborn mammals, (2007), pp. 126-140.
Gomez R. et al, "Probiotics as control agents in aquaculture", Journal of Ocean University of China, (2007), vol. 6, pp. 76-79.
Shi Hn; Walker A., "Bacterial colonization and the development of intestinal defenses", Can. J Gastroenterol, (2004), vol. 18, pp. 493-500, XP002660398.

(Continued)

*Primary Examiner* — Jennifer E Graser
(74) *Attorney, Agent, or Firm* — Katten Muchin Rosenman LLP

(57) ABSTRACT

The invention is directed to a novel strain of *Lactobacillus plantarum* AMT14 and compositions comprising the same.

3 Claims, No Drawings
Specification includes a Sequence Listing.

(56) References Cited

OTHER PUBLICATIONS

Fox SM. Probiotics: "Intestinal Inoculants for Production Animals", Veterinary Medicine (1988); 83, pp. 747-748, 306-810, 824-826, 828-830 (13 pages).

Cai, Hui, et al., Genotypic and phenotypic characterization of Lactobacillus casei strains isolated from different ecologil niches suggests frequent recombination and niche specificity, Microbiology (2007), 153, pp. 2655-2665.

Isa, Jawad Kadhim, et al., "Characterization of Lactobacillus plantarum as a Potential Probiotic In vitro and Use of a Dairy Product (Yogurt) as Food Carrier", Applied Food Biotechnology, 2017, 4 (1): pp. 11-18.

* cited by examiner

STRAIN OF BACTERIA AND COMPOSITION COMPRISING THE SAME

0. SEQUENCE LISTING

The instant application contains a Sequence Listing which has been submitted electronically in ASCII format and is hereby incorporated by reference in its entirety. Said ASCII copy, created on Oct. 18, 2017, is named 383083-00016_SL.txt and is 1,611 bytes in size.

BACKGROUND OF THE INVENTION

1. Field of the Invention

The present inventions is directed to a novel strain of *Lactobacillus plantarum* AMT14 and compositions comprising the same.

*Lactobacillus plantarum* bacterium belongs to lactic acid bacteria, which play an essential role in industry (Patente E., Ciocia F., Ricciardi A., Zotta T., Felis G. E., Torriani S. 2010. Diversity of stress tolerance in *Lactobacillus plantarum, Lactobacillus pentosus* and *Lactobacillus paraplantarum*: a multivariate screening study. International Journal of Food Microbiology 144, 270-279). These bacteria are found commonly in fermented food, olives, cheeses, wine and silages (Tanganurat W., Quniquis B., Leelawatcharams V., Bolotin A., 2009. Genotypic and phenotypic characterization of *Lactobacillus plantarum* strains isolated from Thai fermented fruits and vegetable, Journal Basic Microbiology 49, 377-385). Therefore the strains of this species, having probiotic properties, are applied in functional and therapeutic food production and as potential oral, live vaccines (Shah N. P., 2007. Functional cultures and health benefits. International Dairy Journal 17, 1262-1277).

The mechanism of action of probiotic bacteria is multifactorial and specific for individual strains (Tuohy K. M., Probert H. M., Smejkal C. W, Gibson G. R., 2003. Using probiotics and prebiotics to improve gut health. Drug Discovery 8, 692-700). One of the best known modes of probiotic action against pathogens is an antagonism based on the secretion of bacteriostatic and/or bactericidal substances by probiotics described by Kesarcodi-Watson et al. (Kesarcodi-Watson A., Kaspar H., Lategan M. J., Gibson L., 2008. Probiotics in aquaculture: The need, principles and mechanisms of action and screening processes. Aquaculture, 274, 1-14).

It is believed that the presence of probiotics in the intestine or on skin surface of the host inhibits the growth of potentially pathogenic bacteria (Verschuere L., Heang H., Criel G., Dafnis S., Sorgeloos P., Versraete W., 2000. Protection of Artemia against the pathogenic effects of *Vibrio proteolyticus* CW8T2 by selected bacterial strains. Applied and Environmental Microbiology, 66, 1139-1146).

This antibacterial effect is caused by single substances or in combination with each other, produced by bacteria, such as: antibiotics, bacteriocins, lysozyme, proteases, hydrogen peroxide, ammonia, diacetyl, siderophores, organic acids (Verschuere L. Rombaut G., Sorgeloos P., Verstraete W., 2000. Probiotic bacteria as biological control agents in aquaculture. Microbiology and Molecular Biology Review, 64, 655-671). The effectiveness of antagonism based on secretion of inhibitors to the environment depends mainly on the conditions under which the experimentis run. Biedrzycka et al. (Biedrzycka E, Markiewicz L. H., Bielecka M., Siwicki A. K., 2007, Shaping the micro ecosystem of gastrointestinal tract. Development control of gastrointestinal system in newborn mammals, ed. Zabielski R., Wydawnictwo Rolneli Leśne, 126-140) showed that antagonistic activity of probiotic strains involves not only inhibitor secretion, but also preventing colonisation by probiotic bacteria cells coaggregation with pathogenic cells and competition for the attachment point to the host mucous membranes. Various mechanisms are involved in this process, eg.: electrostatic interactions, hydrophobic influences, lipoteichoic acids (Gómez R., Geovanny D., Balcázar J. L., Shen M, 2007. Probiotics as control agents in aquaculture, Journal of Ocean University of China, 6, 76-79). This properties allow and help bacteria to maintain significant dominance in gastrointestinal track of humans and animals, but dynamic and complex reaction of microorganisms is extremely important for intestine epithelium cells and host's immune system. (Shi H N, Walker A. Bacterial colonization and the development of intestinal defenses, 2004, Can. J Gastroenterol, 18, 493-500). It allows to keep homeostasis and initiates appropriate body response against pathogens.

The gastrointestinal track of human farmed animals (poultry, cattle, pigs, horses, sheep, goats, etc.) may vary in terms of anatomy and function. However, certain similarity of intestinal microflora was found, both in terms of quantity and the presence of the same predominant groups of bacteria. Among microflora colonizing the intestines of animals there are many commensal bacteria, that are pathogenic for animals and cause zoonosis. The most common pathogenic bacteria of animal origin are: *Salmonella, E. coli* O157:H7, *Campylobacter*; and other like *Yersinia enterolitica, Listeria monocytogenes, Bacillus cereus, Staphylococcus aureus, Shigella* spp. and *Clostridium* sp. They can, but not have to be transferred by food of animal origin.

The pioneering work "Intestinal inoculants for production animals" is an overview of available probiotics, applied during livestock farming, including poultry, pigs and calves (Fox Veterinary Medicine, August 1988)

International Publication No. WO 89/05849 discloses bile and acid tolerant bacteria *Lactobacillus* isolated from gastrointestinal track of pigs, which, according to the authors, can be used in milk fermentation. Thus obtained milk is then used to feed piglets in order to prevent diarrhea.

U.S. Pat. No. 5,705,160, European Patent No. 353581, and Polish Patent Nos. 179838, 195089, and PL214583 describe properties of many strains of *Lactobacillus plantarum*, capable of producing large quantities of bacteriostatic substances.

Infections by bacteria *Salmonella* are the most common human food born diseases. Infected products of poultry origin are one of the main sources of infection. Efforts, that are made to control *Salmonella* infections in domestic poultry, result, with few exceptions, from concern for public health, and to a lesser degree, from striving to significant increase of efficiency of poultry production. Therefore it is considered to be reasonable and very desirable to use natural additives in poultry nutrition, what should reduce number of *Salmonella* bacteria in the intestine content.

It has been shown that application of probiotic products has positive impact on skin through their effect on gut-brain-skin axis. According to this, low-fibre diet, stress, antibiotic therapy can cause overgrowth of potentially pathogenic and/or pathogenic microorganisms in the intestine. This results in weakening of intestinal barrier and absorption into the bloodstream of toxic substances, causing inflammation. This can lead to skin lesions aggravation in people predisposed to acne vulgaris, acne erythematosa and allergy. Therefore it is reasonable to apply probiotic bacteria with proved properties in creams and ointments as a specific shield protecting against pathogens. This action is based on inhibition of pathogens colonization present on the skin by blocking their adherence and at the same time by production of antibacterial substances. Moreover, probiotic bacteria inhibit the immune response and consequently reduce skin inflammation. Additionally, they decompose sebum and other skin secretions, which results in easier absorption of nutrients present in the cream.

SUMMARY OF THE INVENTION

The present invention is directed to a novel strain of *Lactobacillum plantarum* AMT14 bacteria which has been deposited under the Budapest Treaty with the Polish Collection of Microorganisms (PCM; Institute of Immunology and Experimental Therapy, Polish Academy of Sciences, ul. Weigla 12, 53-114, Wroclaw, Poland) on Sep. 11, 2015, and has been assigned the accession number B/00092, and compositions comprising the same. In some embodiments, a composition of the present invention comprises *Lactobacillus plantarum* AMT 14 bacteria in an amount of $10^1$ to $10^{13}$ of colony forming units cfu/ml.

In some embodiments, the novel strain of *Lactobacillus plantarum* AMT14 comprises probiotic properties, in particular having bactericidal capacity against potential pathogens and/or pathogens of human and animals. In some embodiments, a strain of the present will have optimal effect on gastrointestinal system as well as on skin of human and animals.

In some embodiments, the novel strain of *Lactobacillus plantarum* AMT14 and composition comprising the same possess outstanding probiotic properties of potentially pathogenic and/or pathogenic bacteria in human and animals, especially considering antagonism against *Salmonella* bacteria, for the preparation of creams, ointments, pharmaceuticals and parapharmaceuticals, food products as well as food and water additives for human and animals.

The strain of *Lactobacillus plantarum* AMT14 has been deposited in the Polish Collection of Microorganisms at The Institute of Immunology and Experimental Therapy, Polish Academy of Sciences in Wrocław, Deposite No B/00092.

DETAILED DESCRIPTION OF THE INVENTION

The Strain Identification

The *Lactobacillus plantarum* AMT14 strain comes from the plant environment. The strain was deposited under the Budapest Treaty in Polish Collection of Microorganisms (PCM) at the Institute of Immunology and Experimental Therapy of Polish Academy of Sciences in Wrocław. The deposit was lodged on Nov. 9, 2015 and the number B/00092 was assigned.

Determination of Species Affiliation of the *Lactobacillus plantarum* AMT14 Strain In order to examine the genre of *Lactobacillus plantarum* AMT14 genotyping was performed using PCR method which involves of application of species-specific primers.

Genotyping Using PCR Method

Identification of the isolated strains was carried out using method of DNA sequencing. The protected material was used for DNA isolation.

DNA Isolation

DNA Isolation was performed according to the procedure:
1. 1 ml of bacterial culture was transferred to an Eppendorf tube and the content was centrifuged (1 min. maximum speed) and the supernatant was poured. This activity was repeated 3 times.
2. To the tube with the cells 100 µl of lysis buffer LT, 10 µl both of proteinase K and lysozyme were added.
3. The tube was incubated at 50° C. for 60 minutes (stirring by vortexing every 15 minutes)
4. After incubation the tube was vigorously vortexed for 20 seconds.
5. The tube was centrifuged for 3 minutes (12 000 rpm, Eppendorf centrifuge)
6. The supernatant was poured to previously described mini-column for DNA purification
7. The test was centrifuged for 1 minute (12 000 rpm, Eppendorf centrifuge)
8. 500 µl of washing solution A1 were added to the mini-column
9. The test was centrifuged for 1 minute (12 000 rpm, Eppendorf centrifuge)
10. The mini-column was transferred to the new tube (2 ml) and 300 µl of washing solution A1 was added to the mini-column.
11. The tube was centrifuged for 3 minutes (12 000 rpm, Eppendorf centrifuge)
12. The mini-column was transferred to the new tube (1.5 ml) and to the sediment on the bottom of mini-column 60 µl of deionised water was added
13. The test was incubated for 5 minutes at room temperature.
14. The test was centrifuged for 1 minute (12 000 rpm, Eppendorf centrifuge)
15. Mini-column was removed and purified DNA in the tube was stored in a refrigerator.
16. DNA quality and DNA quantity was analyzed with spectrophotometric method.

PCR and DNA Sequencing

Isolated DNA was amplified by PCR technique PCR mixture consists of:
1. 10× of DNA polymerase buffer 6 µl
2. MgCl2, 25 mM, 2.4 µl
3. Free nucleotides 2 mM 1.3 µl
4. primer R 20 pmol 0.5 µl
5. primer F 20 pmol 0.5 µl
6. H2O 15 µl
7. DNA polymerase 2u/1 µl 0.15 µl

```
Primer R: 341:
                                           (SEQ ID NO: 1)
5'-CCTACGGGAGGCAGCAG-3'  (Muyzer et al. 1993)

Primer F: 16SR:
                                           (SEQ ID NO: 2)
5'-TACCTTGTTACGACTTCACCCCA-3'  (Rossau et al. 1991)
```

The obtained PCR products were subjected to sequencing reaction, which was carried out in specialized laboratory GENOMED (Warsaw, Ponczowa 12). Elmer ABI 373 Automated DNA Sequencer (PE Applied Biosystems, Foster City, Calif., USA) was used.

The DNA sequence of fragment 16S rRNA of each of five analyzed strains was is:

```
                                           (SEQ ID NO: 3)
GTCTGATGGAGCACGCCGCGTGAGTGAAGAAGGGTTTCGGCTCGTAAAAC

TCTGTTGTTAAAGAAGAACATATCTGAGAGTAACTGTTCAGGTATTGACG

GTATTTAACCAGAAAGCCACGGCTAACTACGTGCCAGCAGCCGCGGTAAT
```

-continued

```
ACGTAGGTGGCAAGCGTTGTCCGGATTTATTGGGCGTAAAGCGAGCGCAG

GCGGTTTTTTAAGTCTGATGTGAAAGCCTTCGGCTCAACCGAAGAAGTGC

ATCGGAAACTGGGAAACTTGAGTGCAGAAGAGGACAGTGGAACTCCATGT

GTAGCGGTGAAATGCGTAGATATATGGAAGAACACCAGTGGCGAAGGCGG

CTGTCTGGTCTGTAACTGACGCTGAGGCTCGAAAGTATGGGTAGCAAACA

GGATTAGATACCCTGGTAGTCCATACCGTAAACGATGAATGCTAAGTGTT

GGAGGGTTTCCGCCCTTCAGTGCTGCAGCTAACGCATTAAGCATTCCGCC

TGGGGAGTACGGCCGCAAGGCTGAAACTCAAAGGAATTGACGGGGGCCCG

CACAAGCGGTGGAGCATGTGGTTTAATTCGAAGCTACGCGAAGAACCTTA

CCAGGTCTTGACATACTATGCAAATCTAAGAGATTAGACGTTCCCTTC.
```

Each of obtained sequences of approximately 650 pz was identical. Comparative analysis with DNA sequences deposited in the Gene Bank (NCBI) indicated that the analyzed sequence is identical with the sequence of *Lactobacillus plantorum*.

Description of Colonies of *Lactobacillus plantarum* AMT14

Colonies of the *Lactobacillus plantarum* AMT14 strain, grown on MRS agar medium (Merck, cat. No. 1106600500) after 48 hours of incubation in relatively anaerobic (microaerophilic) conditions created by applying double layer of MRS agar medium, are of creamy white colour and have spindle shape with length of 1 to 4 mm and a width of 0.5 to 2 mm (at the widest point).

The analysis performed by genotypic method, confirmed that the analysed strain MAT14 belongs to the *Lactobacillus plantarum* species.

In vitro study of antagonistic activity of the *Lactobacillus plantarum* AMT14 strain against pathogenic agents of gastrointestinal track and skin For the study the strains of *Salmonella enterica* subs. *enterica* serovar Enteritidis species were used (the strains: *Salmonella enterica* subsp. *enterica* serovar Enteritidis KOS 64, *Salmonella enterica* subsp. *enterica* serovar Enteritidis 65/s/10) as well as *Esherichia coli* (the strains: *Escherihia coli* O157:H7—enterohemorrhagic strain, *Escherichia coli* Nissle 1917—the strain isolated from the commercial diet supplement called Mutaflor), *Staphylococcus aureus* ATTC 33862.

Pathogenic strains, used in the in vitro tests, came from the National *Salmonella* Centre in Gdynia ((*Salmonella enterica* subsp. *enterica* serovar Enteritidis KOS 64), the Department of Veterinary Hygiene (*Salmonella enterica* subsp. *enterica* serovar Enteritidis 65/s/10—the field strain, isolated from sick birds) and the Institute of Animal Reproduction and Food Research of the Polish Academy of Sciences in Olsztyn (*Escherichia coli* O157:H7, *Escherichia coli* Nissle 1917, *Staphylococcus aureus* ATTC 33862).

The strain of *L. plantarum* AMT14 comes from microorganisms collection which is owned by PROBIOS Ltd. Pathogenic strains were stored as lyophilisate at 4° C. and activated immediately before use by twofold passage in tryptic soy broth (TSB, Merck, cat. No. 1054590500) or in hydrolysed milk.

In order to determine the antimicrobial activity of *L. plantarum* AMT14 bacteria against selected pathogens of *Salmonella enterica* subsp. *enterica* serovar Enteritidis, *Escherichia coli* and *Staphylococcus aureus* species, shared bacterial cultures were performed in hydrolized milk providing good growth of the inhibitory strain of *Lactobacillus plantarum* AMT14 as well as of the inhibited strains of *Salmonella enterica* subsp. *enterica serovar* Enteritidis KOS 64, *Salmonella enterica* subsp. *enterica serovar* Enteritidis 65/s/10, *Escherichia coli* O157:H7, *Escherichia coli* Nissle 1917, *Staphylococcus aureus* ATTC 33862.

Analysis was performed for two different liquid media, ie tryptic soy broth (TSB, Merck, cat. No. 1054590500) and hydrolysed milk in order to assess the impact of the medium on the antimicrobial activity of *Lactobacillus plantarum* AMT14 against the selected pathogens. The experiments were performed applying three independent repeats and then the results were summarized and average values were calculated.

Shared bacterial cultures (research sample) were inoculated using lyophilised *Lactobacillus plantarum* AMT14 strain at a level of $10^9$ colony forming units/ml (described hereinafter by commonly accepted abbreviation cfu/ml) as well as active monoculture of pathogenic strain of *Salmonella enterica* subsp. *enterica serovar* Enteritidis species in an amount of $10^5$ to $10^6$ cfu/ml, *Escherichia coli* in an amount of $10^6$ to $10^7$ cfu/ml, *Staphylococcus aureus* in an amount of $10^5$ cfu/ml. In this experiment, the single pathogenic bacteria strains (*Salmonella enterica* subsp. *enterica serovar* Enteritidis KOS 64, *Salmonella enterica* subsp. *enterica serovar* Enteritidis 65/s/10, *Escherichia coli* O157:H7, *Escherichia coli* Nissle 1917, *Staphylococcus aureus* ATTC 33862) as well as monoculture of *Lactobacillus plantarum* AMT14 were used as control samples applying inoculum level and the liquid medium as in the shared cultures.

The shared cultures as well as single ones were prepared in four parallel tubes in triplicate. Incubation was carried out under aerobic conditions at 37° C. for 0 (inoculum determining blank test) 24, 48 and 72 hours. After the incubation the number of live cells of *Lactobacillus plantarum* bacteria as well as the number of pathogens were determined in shared and control cultures using plate count test on appropriate agar media (Table 1). The analysed material was diluted with 1% peptone water applying the method of serial tenfold dilutions and cultured on the bottom of Petrie dish, then the liquid agar medium at a temperature of 45° C. was poured. Immediately after medium solidifying the plates were inverted upside down and incubated at 37° C. for 24 or 48 hours under aerobic or relatively anaerobic conditions. Conditions of the culture are reported in Table 1.

TABLE 1

Conditions of the cultures of analysed bacterial strains

| the strain type | medium applied | incubation conditions |
| --- | --- | --- |
| *Lactobacillus plantarum* AMT14 | MRS Agar (Merck, cat, No. 1106600500) according to de Man'a J.C, Rogosa M., Sharpe E.M (1960) | 37° C./48 hours, microaerophilic conditions created by applying double layer of MRS agar medium (Merck) |

TABLE 1-continued

Conditions of the cultures of analysed bacterial strains

| the strain type | medium applied | incubation conditions |
|---|---|---|
| *Escherichia coli* O157:H7, *Escherichia coli* Nissle 1917 | Macconkey Agar (Merck, cat. No. 1054650500) | 37° C./24 hours, aerobic conditions |
| *Salmonella enterica* subsp. *enterica* serovar Enteritidis KOS 64, *Salmonella enterica* subsp. *enterica* serovar Enteritidis 65/s/10 | Chromogenic LAB-AGAR Base (BIOCORP, cat. No. PS598) + suplement (BIOCORP, cat. No. SL0061) | 37° C./24 hours, aerobic conditions |
| *Staphylococcus aureus* ATTC 33682 | Braid-Parkera (BTL, cat. No. P-0026) | 37° C./24 hours, aerobic conditions |

After the incubation, bacteria colonies of the shared cultures were counted and compared to the number of bacteria in the control cultures (single ones).

In vitro studies showed total reduction in the number of *Salmonella enterica* subsp. *enterica* serovar Enteritidis KOS64, *Escherichia coli* Nissle 1917 and *Staphylococcus aureus* ATTC 33862 bacteria during 24 hours of incubation, and in the case of shared culture of *Salmonella enterica* subsp. *enterica* serovar Enteritidis 65/s/10 and *Escherichia coli* O157:H7 strains with *Lactobacillus plantarum* AMT14 after 48 hours of incubation total reduction in the number of bacteria was also observed. Neither significantly positive nor negative impact of the medium itself on the result concerning antymicrobial activity of *Lactobacillus plantarum* AMT14 against selected pathogens belonging to the *Salmonella enterica* subsp. *enterica* serovar Enteritidis, *Escherichia coli* and *Staphylococcus aureus* species was observed.

The results are reported in Table 2. In vitro study of antagonistic activity of *Lactobacillus plantarum* AMT14 strain against pathogens of the gastrointestinal tract and skin. The results were presented farther—Table 2.

TABLE 2

An in vitro antagonistic activities of *Lactobacillus plantarum* AMT 14 against pathogens of the gastrointestinal tract and skin

| | *Lactobacillus plantarum* AMT14 | *Escherichia coli* O157:H7 | *Escherichia coli* Nissle1917 | *Salmonella* Enteritidis KOS64 | *Salmonella* Enteritidis 65/s/10 | *Staphylococcus aureus* ATCC33862 |
|---|---|---|---|---|---|---|
| Inokulum | | | | | | |
| *L. plantarum* AMT14 | $1.80 \times 10^9$ | | | | | |
| *E. coli* O157:H7 | | $2.81 \times 10^6$ | | | | |
| *E. coli* Nissle1917 | | | $1.41 \times 10^7$ | | | |
| *S.* Enteritidis KOS64 | | | | $1.24 \times 10^5$ | | |
| *S.* Enteritidis 65/s/10 | | | | | $8.43 \times 10^5$ | |
| *Staphylococcus aureus* ATCC33862 | | | | | | $6.10 \times 10^6$ |
| 24 h of incubation | | | | | | |
| *L. plantarum* AMT14 | $2.76 \times 10^9$ | | | | | |
| *E. coli* O157:H7 | | $5.30 \times 10^8$ | | | | |
| *E. coli* Nissle1917 | | | $9.22 \times 10^8$ | | | |
| *S.* Enteritidis KOS64 | | | | $1.20 \times 10^9$ | | |
| *S.* Enteritidis 65/s/10 | | | | | $6.0 \times 10^8$ | |
| *Staphylococcus aureus* ATCC33862 | | | | | | $2.45 \times 10^8$ |
| 48 h of incubation | | | | | | |
| *L. plantarum* AMT14 | $1.13 \times 10^9$ | | | | | |
| *E. coli* O157:H7 | | $3.20 \times 10^8$ | | | | |
| *E. coli* Nissle1917 | | | $9.46 \times 10^8$ | | | |
| *S.* Enteritidis KOS64 | | | | $2.00 \times 10^8$ | | |
| *S.* Enteritidis 65/s/10 | | | | | $3.2 \times 10^8$ | |
| *Staphylococcus aureus* ATCC33862 | | | | | | $2.24 \times 10^7$ |
| 72 h of incubation | | | | | | |
| *L. plantarum* AMT14 | $2.81 \times 10^8$ | | | | | |
| *E. coli* O157:H7 | | $5.80 \times 10^8$ | | | | |
| *E. coli* Nissle1917 | | | $9.32 \times 10^8$ | | | |
| *S.* Enteritidis KOS64 | | | | $2.77 \times 10^8$ | | |
| *S.* Enteritidis 65/s/10 | | | | | $9.6 \times 10^8$ | |
| *Staphylococcus aureus* ATCC33862 | | | | | | $9.20 \times 10^6$ |

TABLE 2-continued

An in vitro antagonistic activities of *Lactobacillus plantarum* AMT 14 against pathogens of the gastrointestinal tract and skin

| | L. plantarum AMT14 + E. coli O157:H7 | L. plantarum AMT14 + E. coli Nissle1917 | L. plantarum AMT14 + S. Enteritidis KOS64 | L. plantarum AMT14 + S. Enteritidis 65/s/10 | L. plantarum AMT14 + S. aureus ATCC33862 |
|---|---|---|---|---|---|
| Inokulum | | | | | |
| *L. plantarum* AMT14 | $1.80 \times 10^9$ | $1.80 \times 10^9$ | $1.80 \times 10^9$ | $1.80 \times 10^9$ | $1.80 \times 10^9$ |
| *E. coli* O157:H7 | $2.81 \times 10^6$ | | | | |
| *E. coli* Nissle1917 | | $1.41 \times 10^7$ | | | |
| *S. Enteritidis* KOS64 | | | $1.24 \times 10^5$ | | |
| *S. Enteritidis* 65/s/10 | | | | $8.43 \times 10^5$ | |
| *Staphylococcus aureus* ATCC33862 | | | | | $6.10 \times 10^6$ |
| 24 h of incubation | | | | | |
| *L. plantarum* AMT14 | $1.69 \times 10^9$ | $2.51 \times 10^9$ | $1.96 \times 10^9$ | $1.42 \times 10^9$ | $3.18 \times 10^9$ |
| *E. coli* O157:H7 | $1.00 \times 10^1$ | | | | |
| *E. coli* Nissle1917 | | Nb | | | |
| *S. Enteritidis* KOS64 | | | Nb | | |
| *S. Enteritidis* 65/s/10 | | | | $7.50 \times 10^3$ | |
| *Staphylococcus aureus* ATCC33862 | | | | | Nb |
| 48 h of incubation | | | | | |
| *L. plantarum* AMT14 | $5.29 \times 10^8$ | $1.30 \times 10^9$ | $1.40 \times 10^9$ | $8.67 \times 10^8$ | $1.94 \times 10^9$ |
| *E. coli* O157:H7 | Nb | | | | |
| *E. coli* Nissle1917 | | Nb | | | |
| *S. Enteritidis* KOS64 | | | Nb | | |
| *S. Enteritidis* 65/s/10 | | | | Nb | |
| *Staphylococcus aureus* ATCC33862 | | | | | Nb |
| 72 h of incubation | | | | | |
| *L. plantarum* AMT14 | $2.65 \times 10^8$ | $1.25 \times 10^9$ | $2.25 \times 10^8$ | $2.20 \times 10^8$ | |
| *E. coli* O157:H7 | Nb | | | | |
| *E. coli* Nissle1917 | | Nb | | | |
| *S. Enteritidis* KOS64 | | | Nb | | |
| *S. Enteritidis* 65/s/10 | | | | Nb | |
| *Staphylococcus aureus* ATCC33862 | | | | | Nb |

*Nb - absent in 1 ml culture

Determining the Proliferation Ability of *Lactobacillus plantarum* AMT14 at 15° C. and 20° C.

The liquid MRS medium (Merck, cat. No. 1106610500) was inoculated with *Lactobacillus plantarum* AMT14 strain at a dose of approx. $10^7$ colony forming units/ml. The culture was carried out in three parallel tubes under aerobic conditions at temperatures 15° C. and 20° C. for 24, 48 and 72 hours. In addition, parallel control culture of the analysed strain was carried out under aerobic condition at an optimal growth temperature, i.e., 37° C. The number of live cells was determined immediately after inoculation and after 24, 48 and 72 hours. Bacteria incubation was performed on Petri dishes at 37° C. for 48 hours under relatively anaerobic conditions. Parallel to the cells number determination, the potentiometric measurement of pH level of the culture was performed.

The strain of *Lactobacillus plantarum* AMT14 showed ability to grow at 15° C. and 20° C. The analysed strain of *Lactobacillus plantarum* AMT14 proliferated slightly slower in the first day of incubation at 15° C., then it reached the number of $1.4 \times 10^8$ colony forming units/ml (described hereinafter by commonly accepted abbreviation cfu/ml), referring to the parallel control culture—$1.5 \times 10^9$ cfu/ml. In the 48th and 72nd hour of incubation the strain population was of $1.6 \times 10^9$ and $2.3 \times 10^9$ cfu/ml respectively. However, in the case of control culture each day of incubation resulted in reduction of the cells number to the level of $10^8$ cfu/ml. In contrast, the population of *L. plantarum* AMT14 at 20° C. was comparable to the cells number that strain AMT14 reached at optimal growth temperature, i.e., 37° C. After 24 hours and 48 hours of incubation at 20° C. the strain population was $2.0 \times 10^9$ and $2.9 \times 10^9$ cfu/ml respectively and in the next 24 hours of incubation remained unchanged.

TABLE 3

Determination of growth ability of the *Lactobacillus plantarum* AMT14 strain at 15° C. and 20° C.

| | The number of bacteria of *Lactobacillus plantarum* AMT14 (cfu/ml) | | | |
|---|---|---|---|---|
| Strain | inoculum | 24 h of incubation | 48 h of incubation | 72 h of incubation |
| *Lactobacillus plantarum* AMT14 (control culture, incubation at 37° C.) | $1.8 \times 10^7$ | $1.5 \times 10^9$ | $6.3 \times 10^8$ | $2.3 \times 10^8$ |
| *Lactobacillus plantarum* AMT14 (incubation at 15° C.) | $1.8 \times 10^7$ | $1.4 \times 10^8$ | $1.6 \times 10^9$ | $2.3 \times 10^9$ |
| *Lactobacillus plantarum* AMT14 (incubation at 20° C.) | $1.8 \times 10^7$ | $2.0 \times 10^9$ | $2.9 \times 10^9$ | $2.9 \times 10^9$ |

It was found that the strain of *Lactobacillus plantarum* AMT14 has unique properties to growth at low temperatures, i.e., below 16° C.

Determination of Survivability of *Lactobacillus plantarum* AMT14 Strain at Low pH as Well as in the Presence of Bile Salts.

The survivability of *Lactobacillus plantarum* AMT14 strain at low pH was determined by acidity reduction of *Lactobacillus plantarum* AMT14 culture being in stationary phase of growth to a pH value of 3. However, in the case of survivability determination of *Lactobacillus plantarum* AMT14 strain in the presence of bile salts, at the beginning pH of *Lactobacillus plantarum* AMT14 culture was raised to a value of 6, then bile salts in an amount of 3% of the culture were added. Determination of survivability of *Lactobacillus plantarum* AMT14 strain at low pH was performed before lowering the pH of the culture (control sample), just after lowering the pH of the culture to a value of 3, so called minute 0, and after 40 and 180 minutes of incubation at 37° C. under anaerobic conditions. The survivability of *Lactobacillus plantarum* AMT14 in the presence of bile salts was determined prior to bile salts addition (control sample), just after addition of bile salts, so called minute 0 and after 1, 3 and 6 hours of incubation at 37° C. under anaerobic conditions. The live cells of *Lactobacillus plantarum* AMT14 was determined in colony forming units (cfu/ml) following the pure plate method.

The survivability of *Lactobacillus plantarum* AMT14 strain was expressed as a percentage of the number of *Lactobacillus plantarum* AMT14 after 180 minutes in the case of survivability determining at pH value of 3, and after 6 hours in the case of the number determination of *Lactobacillus plantarum* AMT14 in the presence of bile salts. The obtained results were compared respectively to the number of *Lactobacillus plantarum* AMT14 strain in control sample.

TABLE 4

Survivability of *Lactobacillus plantarum* AMT14 strain at pH = 3

| Strain | Number of bacteria (log10 cfu/ml) | | | | Survivabilty after 180 minutes % |
|---|---|---|---|---|---|
| | before pH lowering 0 minute | pH = 3 0 minute | 40 minutes | 180 minustes | |
| *Lactobacillus plantarum* AMT14 | 8.95 | 9.08 | 9.07 | 8.98 | 100 |

TABLE 5

Survivability of *Lactobacillus plantarum* AMT14 strain in the presence of bile salts in amount of 3%

| Szczep | Number of bacteria (log10 cfu/ml) | | | | | Survivability after 6 hours % |
|---|---|---|---|---|---|---|
| | before addition of bile salts | after addition of bile salts | | | | |
| | | 0 h | 1 h | 3 h | 6 h | |
| *Lactobacillus plantarum* AMT14 | 9.03 | 8.92 | 8.70 | 8.03 | 8.05 | 89 |

The examined strain of *Lactobacillus plantarum* AMT14 showed 100% of survivability at low pH=3 and 89% of survivability in the presence of 3% of bile salts.

The results showed high resistance of *Lactobacillus plantarum* AMT14 at low pH as well as in the presence of bile salts. This indicates that the *Lactobacillus plantarum* AMT14 strain adapts to the conditions of gastrointestinal tract.

---

What is claimed is:

1. A composition comprising a strain of *Lactobacillus plantarum* AMT 14 bacteria (PCM Accession No. B/00092) in an amount of $10^1$ to $10^{13}$ of colony forming units cfu/ml, a medium, and a bulking agent.

2. The composition of claim 1, wherein the composition is a cream, an ointment, a parapharmaceutical, a pharmaceutical, a food preparation, or a food and/or water additive for humans or animals.

3. The composition of claim 1, comprising a lyophilised strain of *Lactobacillus plantarum* AMT14 and a medium.

* * * * *

SEQUENCE LISTING

<160> NUMBER OF SEQ ID NOS: 3

<210> SEQ ID NO 1
<211> LENGTH: 17
<212> TYPE: DNA
<213> ORGANISM: Lactobacillus plantarum
<220> FEATURE:
<223> OTHER INFORMATION: Primer R: 341

<400> SEQUENCE: 1
cctacgggag gcagcag                                                    17

<210> SEQ ID NO 2
<211> LENGTH: 23
<212> TYPE: DNA
<213> ORGANISM: Lactobacillus plantarum
<220> FEATURE:
<223> OTHER INFORMATION: Primer F: 16SR

<400> SEQUENCE: 2
taccttgtta cgacttcacc cca                                             23

<210> SEQ ID NO 3
<211> LENGTH: 648
<212> TYPE: DNA
<213> ORGANISM: Lactobacillus plantarum
<220> FEATURE:
<223> OTHER INFORMATION: 16SrRNA

```
<400> SEQUENCE: 3
gtctgatgga gcacgccgcg tgagtgaaga agggtttcgg ctcgtaaaac tctgttgtta      60
aagaagaaca tatctgagag taactgttca ggtattgacg gtatttaacc agaaagccac     120
ggctaactac gtgccagcag ccgcggtaat acgtaggtgg caagcgttgt ccggatttat     180
tgggcgtaaa gcgagcgcag gcggtttttt aagtctgatg tgaaagcctt cggctcaacc     240
gaagaagtgc atcggaaact gggaaacttg agtgcagaag aggacagtgg aactccatgt     300
gtagcggtga aatgcgtaga tatatggaag aacaccagtg gcgaaggcgg ctgtctggtc     360
tgtaactgac gctgaggctc gaaagtatgg gtagcaaaca ggattagata ccctggtagt     420
ccataccgta aacgatgaat gctaagtgtt ggagggtttc cgcccttcag tgctgcagct     480
aacgcattaa gcattccgcc tggggagtac ggccgcaagg ctgaaactca aaggaattga     540
cgggggcccg cacaagcggt ggagcatgtg gtttaattcg aagctacgcg aagaacctta     600
ccaggtcttg acatactatg caaatctaag agattagacg ttcccttc                  648
```